US010638928B2

(12) United States Patent
Yamanaka (10) Patent No.: US 10,638,928 B2
(45) Date of Patent: May 5, 2020

(54) MEASUREMENT PROBE, MEASUREMENT DEVICE, AND ATTACHMENT MECHANISM (71) Applicant: Sharp Life Science Coporation, Kobe, Hyogo (JP)

(72) Inventor: Mikihiro Yamanaka, Sakai (JP)

(73) Assignee: Sharp Life Science Corporation, Kobe (JP)

(*) Notice: Subject to any disclaimer, the term of this patent is extended or adjusted under 35 U.S.C. 154(b) by 505 days.

(21) Appl. No.: 15/314,208

(22) PCT Filed: May 18, 2015

(86) PCT No.: PCT/JP2015/064240
§ 371 (c)(1),
(2) Date: Nov. 28, 2016

(87) PCT Pub. No.: WO2015/182428
PCT Pub. Date: Dec. 3, 2015

(65) Prior Publication Data
US 2017/0188827 A1 Jul. 6, 2017

(30) Foreign Application Priority Data

May 29, 2014 (JP) ................................. 2014-111554

(51) Int. Cl.
A61B 5/1455 (2006.01)
A61B 5/00 (2006.01)
(Continued)

(52) U.S. Cl.
CPC .............. A61B 5/00 (2013.01); A61B 5/0071 (2013.01); A61B 5/0261 (2013.01);
(Continued)

(58) Field of Classification Search
CPC ..... A61B 5/00; A61B 5/0071; A61B 5/02416; A61B 5/0261; A61B 5/14546;
(Continued)

(56) References Cited

U.S. PATENT DOCUMENTS 1,080,308 A * 12/1913 Stewart ................... G01P 21/02
73/1.37
4,646,722 A * 3/1987 Silverstein ......... A61B 1/00073
600/104
(Continued)

FOREIGN PATENT DOCUMENTS

CN 103565410 A 2/2014
JP 2004-267613 A 9/2004
(Continued)

OTHER PUBLICATIONS

Kitamura et al., "Optical constants of silica glass from extreme UV to far IR at near room temperature", Applied Optics, vol. 46, No. 33, pp. 8118-8133, 2007.*
(Continued)

Primary Examiner — Eric F Winakur
Assistant Examiner — Chu Chuan Liu
(74) Attorney, Agent, or Firm — ScienBiziP, P.C.

(57) ABSTRACT

Provided is a measurement probe of which hygiene can be easily secured. The measurement probe (1) receives fluorescence emitted by radiation of excitation light to a fingertip (90). The measurement probe (1) includes: a radiating portion that radiates the excitation light; a light-receiving portion that receives the fluorescence; a sleeve (16) disposed at a front end portion of the radiating portion or the light-receiving portion; and a transparent quartz plate (15) disposed at a front end surface (14I) of the radiating portion or
(Continued)

the light-receiving portion. The sleeve (16) is provided with an opening in which the quartz plate (15) is detachably mounted.

5 Claims, 8 Drawing Sheets

(51) Int. Cl.
  *A61B 5/145* (2006.01)
  *A61B 5/024* (2006.01)
  *A61B 5/026* (2006.01)
  *A61B 10/02* (2006.01)

(52) U.S. Cl.
  CPC ........ *A61B 5/02416* (2013.01); *A61B 5/1455* (2013.01); *A61B 5/14546* (2013.01); *A61B 5/14556* (2013.01); *A61B 5/6826* (2013.01); *A61B 10/02* (2013.01); *A61B 2560/0462* (2013.01); *A61B 2562/0233* (2013.01); *A61B 2562/146* (2013.01)

(58) Field of Classification Search
  CPC . A61B 5/1455; A61B 5/14556; A61B 5/6826; A61B 10/02; A61B 2560/0462; A61B 2562/0233; A61B 2562/146
  See application file for complete search history.

(56) References Cited

U.S. PATENT DOCUMENTS

| | | | | |
|---|---|---|---|---|
| 4,794,911 | A * | 1/1989 | Okada | A61B 1/00096 600/127 |
| 5,408,998 | A * | 4/1995 | Mersch | A61B 1/042 600/333 |
| 5,697,373 | A * | 12/1997 | Richards-Kortum | A61B 5/0071 356/301 |
| 6,006,119 | A * | 12/1999 | Soller | A61B 5/14535 356/39 |
| 6,152,876 | A * | 11/2000 | Robinson | A61B 5/14532 252/408.1 |
| 2008/0152347 | A1* | 6/2008 | Chen | A63F 13/02 398/107 |
| 2013/0110311 | A1* | 5/2013 | Ver Steeg | G01N 21/27 701/1 |
| 2013/0123642 | A1 | 5/2013 | Yamaguchi et al. | |
| 2013/0168573 | A1 | 7/2013 | Yamanaka et al. | |
| 2013/0253338 | A1 | 9/2013 | Kang et al. | |
| 2013/0281865 | A1 | 10/2013 | Kang et al. | |
| 2014/0163387 | A1 | 6/2014 | Kang et al. | |

FOREIGN PATENT DOCUMENTS

| | | |
|---|---|---|
| JP | 2007-510159 A | 4/2007 |
| JP | 2009-066042 A | 4/2009 |
| JP | 2012-058104 A | 3/2012 |
| JP | 2013-134243 A | 7/2013 |
| JP | 2013-192958 A | 9/2013 |
| JP | 2013-195433 A | 9/2013 |
| JP | 2013-248359 A | 12/2013 |
| WO | 2005/045393 A2 | 5/2005 |
| WO | 2011/114653 A1 | 9/2011 |

OTHER PUBLICATIONS

Yoder, "Mounting Optical Components", Chp 37, Handbook of Optics, pp. 37.1-37.26, 1995.*
Thorlabs, Drawing: Part F230FC-1550, dated Aug. 16, 2010.*
Official Communication issued in International Patent Application No. PCT/JP2015/064240, dated Aug. 4, 2015.

* cited by examiner

RELATIONSHIP BETWEEN WAVELENGTH OF EXCITATION LIGHT AND WAVELENGTH OF FLUORESCENCE IN AGEs

|  | EXCITATION LIGHT (nm) | FLUORESCENCE (nm) |
|---|---|---|
| COLLAGEN-LINKED FLUORESCENCE (CLF) | 370 | 440 |
| PENTOSIDINE | 328 (AFTER ACID HYDROLYSIS: 335) | 378 (AFTER ACID HYDROLYSIS: 385) |
| VESPERLYSINE | 370 | 440 |

MEASUREMENT PROBE, MEASUREMENT DEVICE, AND ATTACHMENT MECHANISM

TECHNICAL FIELD

The present invention relates to a measurement probe that receives fluorescence emitted from fluorescent substances in a biological sample.

BACKGROUND ART

In recent years, a grave problem arises in medical and social fields in that patients with lifestyle-related diseases increase as diets are westernized. Currently, it is reported that there are eight million diabetic patients and there are twenty million diabetes-related people when would-be diabetic patients are included. Three major complications of diabetes are "retinopathy, nephropathy, and neuropathy", and the diabetes develops as a factor of arteriosclerosis, and thus there is a concern that the diabetes will develop to a heart disease or a brain disease.

The diabetes develops when a function of the pancreas is degraded due to disorder of a diet habit or a lifestyle, an influence of secretions from adipose cell because of obesity, and oxidative stress, and then an amount of insulin that controls a blood glucose level is insufficient, or efficacy of the insulin is lowered. The diabetes brings about symptoms of an increase in the number of times or an amount of urination, a dry throat, or the like; however, the symptoms do not develop to a subjective symptom of a disorder, and thus the diabetes are mostly diagnosed through an examination in a hospital or the like. This is why there are many "silent" diabetic patients.

When abnormal symptoms appear due to the complications and are examined in a hospital or the like, disease conditions are already developed in many cases, and thus it is difficult to completely cure the disease. In particular, it is often difficult to perform medical treatment on the complications, and thus it is important to prevent diabetes, similarly to other lifestyle-related diseases. In order to perform the prevention, it is inevitable to recognize the diabetes early and to determine treatment effects. In this respect, there are many examination methods of the diabetes.

Under a condition in which there are an abnormal amount of carbohydrates or lipids in blood, application of oxidative stress results in a reaction between proteins and the carbohydrates or the lipids, and advanced glycation endproducts (AGEs) are produced. The AGEs are end products that are formed in a nonenzymatic glycosylation reaction (Maillard reaction) of proteins, have a yellowish brown color, are substances which emit fluorescence, and have a property of being linked to proteins in the vicinity thereof and forming cross-linkage.

The AGEs are known to be deposited or infiltrate in blood vessel walls, or to cause inflammation by acting on macrophages which are a part of an immune system and releasing cytokines as a kind of proteins, and thus to induce arteriosclerosis.

In the case of the diabetes, the AGEs increase as the blood glucose increases. Therefore, monitoring of the AGEs makes it possible to recognize diabetes early or to find a development state. As described above, as a method for screening diabetes mellitus by monitoring the AGEs, for example, a method disclosed in PTL 1 is reported.

In the method, the skin on a forearm is illuminated with excitation light, a fluorescence spectrum from the AGEs linked to skin collagen is measured, and the measured fluorescence spectrum is compared to a predetermined model. In this manner, the AGEs are monitored. As described above, data of the AGEs are acquired without invasion.

CITATION LIST

Patent Literature

PTL 1: Japanese Unexamined Patent Application Publication (Translation of PCT Application) No. 2007-510159 (published Apr. 19, 2007)

SUMMARY OF INVENTION

Technical Problem

In the method disclosed in PTL 1, a measurement probe (optical probe) that receives fluorescence derived from AGEs excited by radiation of excitation light to a living body (or a biological sample) is used. Therefore, the forearm (measurement target site) of a subject is brought into contact with a front end of the measurement probe, and thereby the measurement probe receives fluorescence.

However, in PTL 1, a configuration for hygienically using a measurement probe that receives fluorescence derived from the AGEs excited by radiation of the excitation light to a living body is not considered.

Therefore, whenever forearms (measurement target sites) of subjects are brought into contact with the front end of the measurement probe such that measurement is performed, the front end of the measurement probe needs to be cleaned with an alcohol or the like. Hence, a problem arises in that it is not possible to easily secure hygiene of the measurement probe.

The present invention is made to solve the problem described above, and thus an object thereof is to provide a measurement probe of which hygiene can be easily secured.

Solution to Problem

In order to solve the problem described above, a measurement probe according to an aspect of the present invention is a measurement probe that receives fluorescence emitted by radiation of excitation light to a biological sample. The measurement probe includes: a radiating portion that radiates the excitation light; a light-receiving unit that receives fluorescence; a support member disposed at a front end portion of the radiating portion or the light-receiving portion; and a transparent protective member disposed at a front end surface of the radiating portion or the light receiving portion. The support member is provided with an opening in which the protective member is detachably mounted.

Advantageous Effects of Invention

According to an aspect of the present invention, an effect is achieved in that it is possible to easily secure hygiene of the measurement probe.

BRIEF DESCRIPTION OF DRAWINGS

FIGS. 1(a) and 1(b) are diagrams illustrating a detailed configuration of a measurement probe according to Embodiment 1 of the present invention, where

FIGS. 5(a) and 5(b) are diagrams illustrating a detailed configuration of a measurement probe as a comparative example of Embodiment 1 of the present invention, where

FIGS. 8(a) and 8(b) are diagrams illustrating a detailed configuration of a measurement probe according to Embodiment 2 of the present invention, where

FIGS. 9(a) and 9(b) are diagrams illustrating a detailed configuration of a measurement probe according to Embodiment 3 of the present invention, where

FIGS. 10(a) and 10(b) are diagrams illustrating a detailed configuration of a measurement probe according to Embodiment 4 of the present invention, where

DESCRIPTION OF EMBODIMENTS

Embodiment 1

Embodiment 1 of the present invention is described on the basis of FIGS. 1 to 7, as follows.

(Measurement Device 1)

Figure 1:
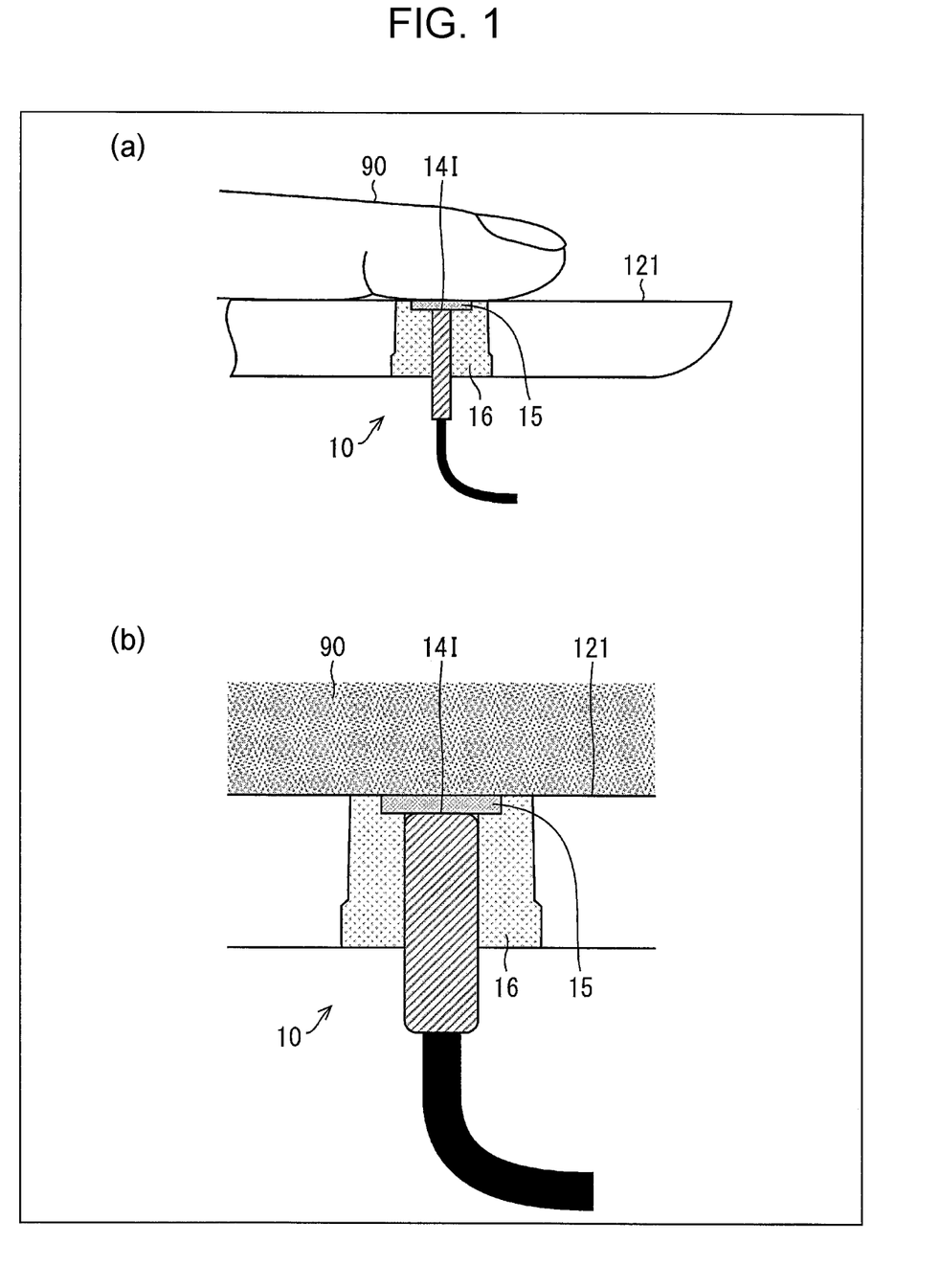
FIG. 1(a) is a diagram illustrating a state in which a fingertip is placed on a measurement base.
FIG. 1(b) is an enlarged diagram of the vicinity of a front end surface of the measurement probe.
Figure 2:
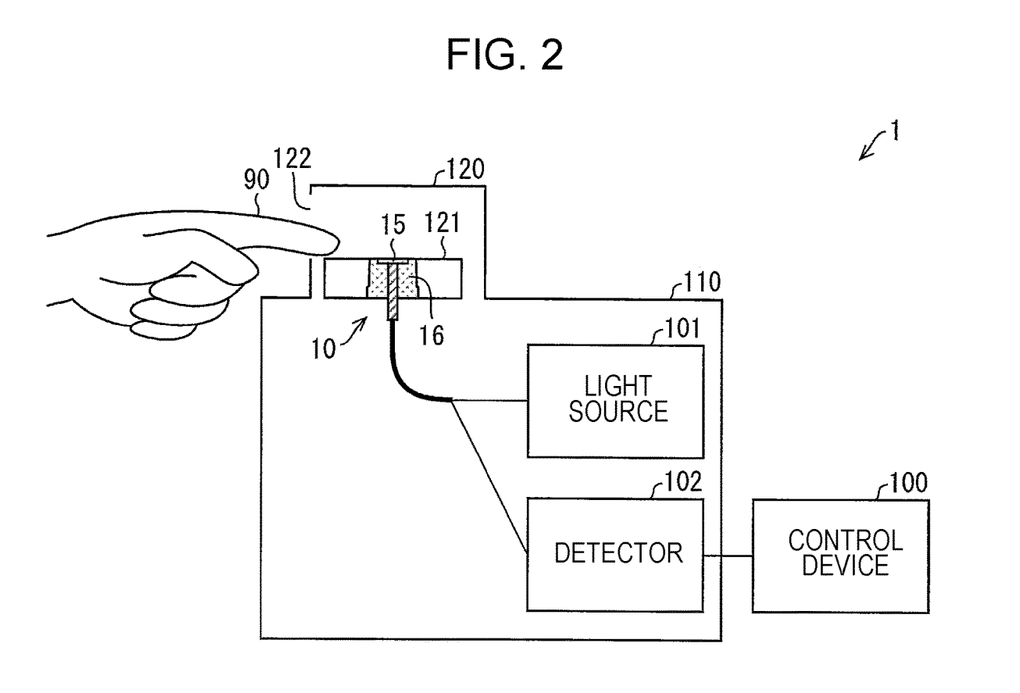
FIG. 2 is a diagram illustrating a configuration of the measurement device according to Embodiment 1 of the present invention.

FIG. 2 is a diagram illustrating a configuration of a measurement device 1 according to the embodiment. The measurement device 1 includes a control device 100 and a measuring-member disposing unit 110. FIG. 1 illustrates a configuration in which a fingertip 90 (biological sample) of a subject is a measurement target site, and fluorescence derived from AGEs in a blood vessel of the fingertip is measured.

However, the measurement target site, in which the fluorescence derived from the AGEs is detected, may not be necessarily limited to the fingertip 90, but may be a part of a living body (a part of a site of a body of a subject). For example, the measurement target site may be an arm, a wrist, or the like of the subject.

Further, the target, in which the fluorescence derived from AGEs is detected, may be living tissue which is obtained by sampling from a part of a living body and of which biological activity is stopped. Thus, it is possible for a measurement target of the measurement device 1 to include various biological samples as evaluation targets through a biopsy.

(Measuring-Member Disposing Unit 110)

The measuring-member disposing portion 110 includes a measurement probe 10, a light source 101, and a detector 102 (detecting unit). In other words, the measuring-member disposing unit 110 includes a member for measuring the fluorescence derived from the AGEs.

The measuring-member disposing unit 110 is provided with a fingertip inserting portion 120. The fingertip inserting portion 120 has an insertion hole 122. The insertion hole 122 is an opening that forms a space for inserting the fingertip 90 of the subject inside the measurement device 1.

The measuring-member disposing unit 110 has a measurement base 121. The measurement base 121 is a member on which the fingertip 90 of the subject is placed. The measurement base 121 is disposed in a portion that communicates with the fingertip inserting portion 120.

The measurement base 121 is provided with a hole having a diameter of 5 to 10 mm so that excitation light is extracted from the measurement probe 10 to be described below. The measurement probe 10 including a quartz plate 15 (protective member) and a sleeve 16 (support member, that is, a first support member) to be described below is inserted into the hole.

Note that, in a case where the measurement target site is the arm, the wrist, or the like of the subject, it may not be necessary to provide the fingertip inserting portion 120.

(Schematic Configuration of Measurement Probe 10)

Figure 3:
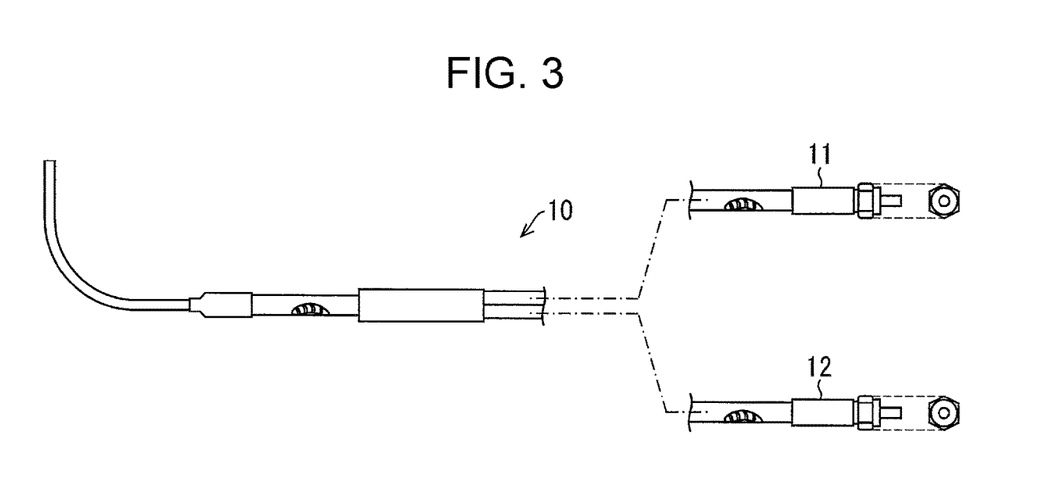
FIG. 3 is a diagram illustrating a schematic configuration of the measurement probe according to Embodiment 1 of the present invention.

FIG. 3 is a diagram illustrating a schematic configuration of the measurement probe 10. The measurement probe 10 functions as a radiating portion that radiates the excitation light to the measurement target site, and as a light-receiving portion that receives fluorescence emitted by radiation of the excitation light to the measurement target site. In other words, the measurement probe 10 combines the radiating portion and the light-receiving portion.

As illustrated in FIG. 3, the measurement probe 10 includes light incoming/light emitting coaxial optical fibers. Specifically, the measurement probe 10 includes a light incoming fiber 11 (radiating portion) that guides the excitation light from the light source 101 to the measurement target site, and a light emitting fiber 12 (light-receiving portion) that guides the fluorescence emitted in the measurement target site to the detector 102.

One end portion (front end surface 14I in FIG. 1, which will be described below) of the measurement probe 10 on a side, where the light incoming fiber 11 and the light emitting fiber 12 form a single unit, is inserted into the hole provided in the measurement base 121.

In addition, the light incoming fiber 11 and the light emitting fiber 12 are separated from each other at the other end portion, the light incoming fiber 11 is connected to the light source 101, and the light emitting fiber 12 is connected to the detector 102.

In this manner, it is possible for the excitation light to radiate toward the measurement target site, and it is possible to guide the fluorescence emitted from the measurement target site to the detector 102. The detection of the fluorescence enables the measurement device 1 to non-invasively measure an amount of the AGEs that is present in a blood vessel.

Note that, in the measurement probe 10, it may not be necessary that the light incoming fiber 11 and the light emitting fiber 12 be provided to be the coaxial fibers, but the fibers may be provided as separate fibers. Hence, only one of the radiating portion or the light-receiving portion may be disposed on the front end surface 14I of the measurement probe 10.

(Light Source 101)

The light source 101 is a light source that emits the excitation light that radiates to the measurement target site. The excitation light is to detect the fluorescence derived from the AGEs and has an appropriate wavelength range so as to excite the AGEs.

As types of light sources 101 which are used as the light source 10, it is possible to use a bulb type of light source such as a halogen light source or a xenon light source, a light-emitting diode (manufactured by Nichia Corporation, by DOWA Electronics Materials Co., Ltd., or the like), a laser diode, or the like.

Figure 4:
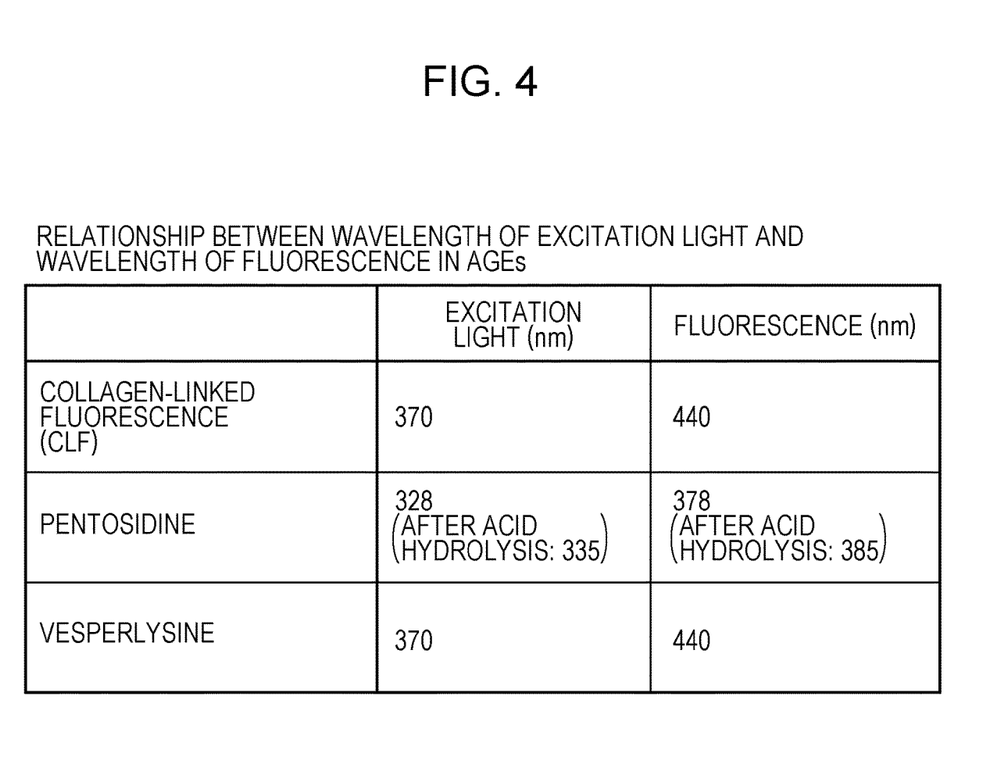
FIG. 4 is a diagram illustrating a relationship between a wavelength of excitation light and a wavelength of fluorescence in AGEs.
Figure 5:
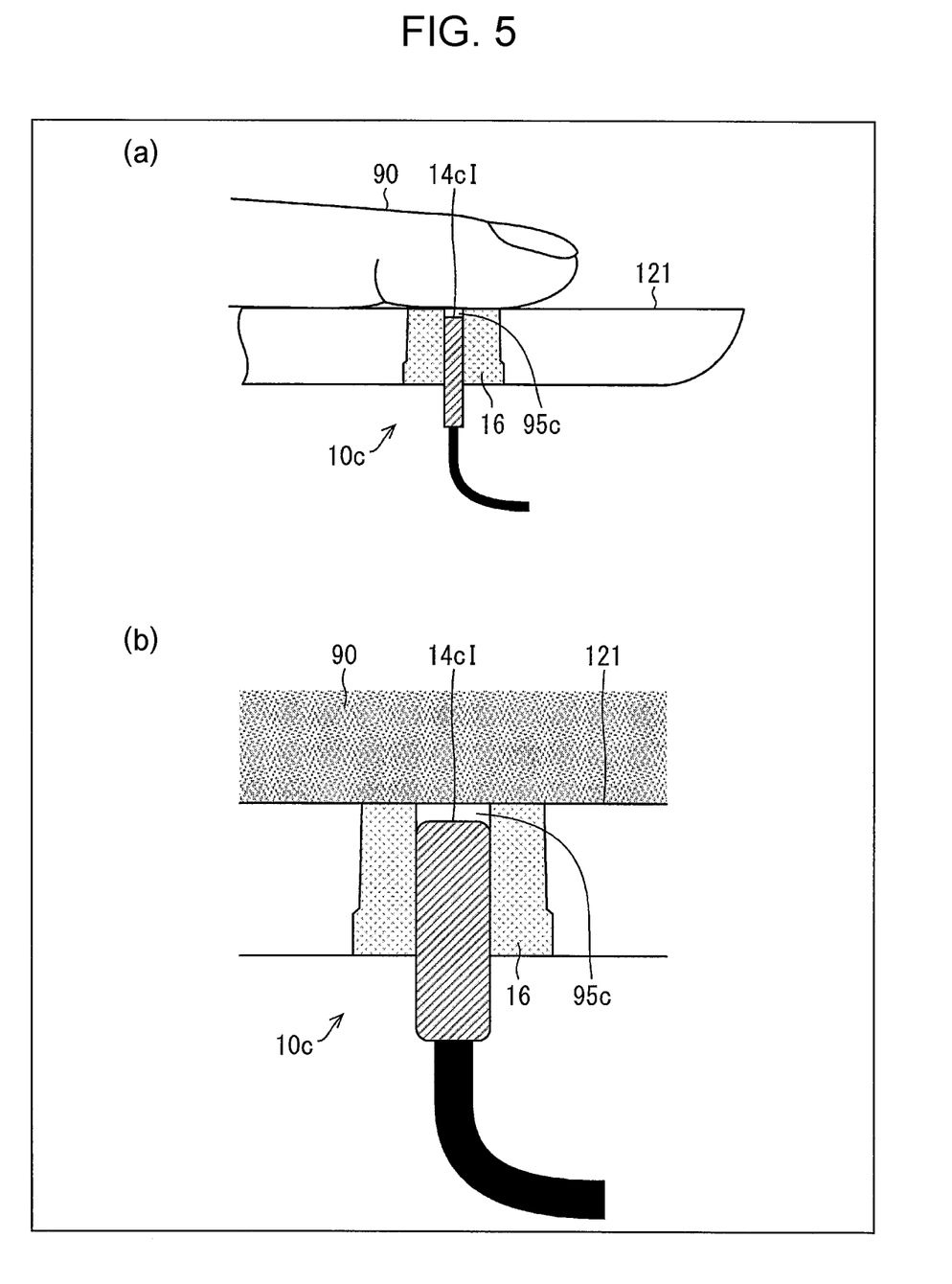
FIG. 5(a) is a diagram illustrating a state in which a fingertip is placed on a measurement base.
FIG. 5(b) is an enlarged diagram of the vicinity of a front end surface of the measurement probe.

FIG. 4 is a table showing a relationship between a wavelength of excitation light and a wavelength of fluorescence in AGEs. There are about 20 types of AGEs known at present. Several types of AGEs emit fluorescence when receiving radiation of the excitation light. Hereinafter, the wavelength range of the excitation light emitted from the light source 101 is described with reference to FIG. 4.

Collagen-linked fluorescence (CLF) means fluorescence from the AGEs linked to collagen. The CLF is used as a general criterion of total production of the AGEs and collagen cross-linking associated therewith.

Pentosidine and vesperlysine are typical examples of the AGEs. The pentosidine has a structure in which lysine having moles equal to pentose is cross-linked to arginine and is converted into is a fluorescent substance which is stable after acid hydrolysis. In particular, the pentosidine is reported to increase in the development of diabetes or terminal nephropathy.

In addition, the vesperlysine is isolated as a major fluorescent substance after the acid hydrolysis of AGE-converted bovine serum albumin (BSA) is performed, and has a structure in which two molecules of lysine are cross-linked. Note that, examples of the AGEs not illustrated in FIG. 4 may include glucosepane or the like.

As understood in FIG. 4, the excitation light emitted from the light source 101 most preferably has a wavelength of 365 nm or a wavelength approximate to 365 nm. However, an appropriate wavelength range of the excitation light varies depending on the types of AGEs.

Therefore, it is preferable that the light source 101 emit excitation light having a wavelength range of 315 nm to 400 nm, which is a region of a UVA. Further, it is more preferable that the light source 101 emit excitation light having a wavelength range of 315 nm to 600 nm, which includes a wavelength range of visible light.

(Detector 102)

The detector 102 receives the fluorescence emitted by radiation of the excitation light to the measurement target site, and measures the wavelength of the fluorescence and a fluorescence intensity for each wavelength. In other words, the detector 102 detects how strong the detected fluorescences having certain wavelengths.

As the detector 102, it is possible to use a CCD detector (ILX511B: by Sony Corporation), a photodetector (Si PIN photodiode: by Hamamatsu Photonics K.K.), a semiconductor detector such as a CMOS image sensor, a photomultiplier tube (PMT), a channeltron detector, or the like.

As understood in FIG. 4, the fluorescence has a wavelength longer than the excitation light. Therefore, the detector 102 which may detect light in the range of 350 nm to 500 nm is used. However, the wavelength of fluorescence varies depending on types of AGEs.

Therefore, it is preferable that the detector 102 detects light in the range of 320 nm to 900 nm. Note that the detector 102 may include an optical spectrometer.

(Control Device 100)

The control device 100 collectively controls an operation of the measurement device 1. Specifically, the control device 100 performs processes of luminance adjustment of excitation light emitted from the light source 101, switching control between the radiation or non-radiation of the excitation light, storage of data, display of data, data analysis, or the like. The control device 100 may be realized by a personal computer (PC), for example.

In addition, the control device 100 displays, on a monitor (not illustrated), a fluorescence spectrum obtained, based on detection results (fluorescence intensity for each wavelength) input from the detector 102.

Further, the control device 100 may calculate an amount of accumulation of fluorescence substances such as the AGEs that are accumulated on the blood vessel wall of the measurement target site, on the basis of the detection result input from the detector 102.

The control device 100 may convert the calculated amount of fluorescence substance into an index (for example, five stages of health condition levels) which shows a health condition of the subject and display the index on the monitor, and thereby providing information which is easy to be understood by the subject.

(Detailed Configuration of Measurement Probe 10)

Next, a detailed configuration of the measurement probe 10 is described with reference to FIGS. 1(a) and 1(b). FIG. 1(a) is a view illustrating a state in which the fingertip 90 is placed on the measurement base 121. FIG. 1(b) is an enlarged view illustrating the vicinity of the front end surface 14I of the measurement probe 10 in FIG. 1(a).

As will be described below, the measurement probe 10 includes the quartz plate 15 and the sleeve 16. The top surface (surface closest to the measurement target site) of the quartz plate 15 is provided to come into contact with the fingertip 90 during the measurement of the fingertip 90. In addition, the bottom surface (surface on a side opposite the top surface) of the quartz plate 15 comes into contact with the front end surface 14I.

Therefore, the quartz plate 15 serves as a protective member that protects the front end surface 14I during the contact with the fingertip 90. In addition, the quartz plate 15 has a refractive index higher than air. Therefore, a difference between the refractive index of the quartz plate 15 and a refractive index of the front end surface 14I is relatively small.

The sleeve 16 is provided at the front end portion of the measurement probe 10 so as to surround the front end surface 14I in a circumferential direction. The sleeve 16 may be made of a transparent acrylic material, for example.

The front end of the sleeve 16 projects from the front end surface 14I. Hence, the front end surface 14I is disposed at a position more separated from the fingertip 90, compared to the front end of the sleeve 16. Note that a dimension of an amount of projection of the front end of the sleeve 16 (a distance from the front end of the sleeve 16 to the front end surface 14I) is about 1 mm (0.5 mm to 2 mm).

As described above, the sleeve 16 is provided with an opening through which the quartz plate 15 is detachably mounted. Hence, the sleeve 16 serves as a support member that supports the quartz plate 15 in the circumferential direction of the opening.

The quartz plate 15 is provided, and thereby it is possible to prevent the fingertip 90 from coming into direct contact with the front end surface 14I. Therefore, it is possible for the front end surface 14I to be kept clean.

Note that, in order for the measurement probe 10 to perform measurement, it is necessary that the protective member has a property of transmitting the excitation light radiating toward the fingertip 90 from the front end surface 14I, and the fluorescence emitted from the fingertip 90. Therefore, the quartz plate 15 is made of a member having optical transparency (light transmission).

In the measurement probe 10 of the embodiment, a thickness of the quartz plate 15 is about 1 mm (0.5 mm to 2 mm). However, the thickness of the quartz plate 15 is not particularly limited, and the thickness may be appropriately determined depending on optical specifications of the measurement probe 10. Note that, in the measurement probe 10 of the embodiment, the quartz plate 15 is formed to have a plate shape with a cross-sectional plane of a substantially rectangular shape.

Quartz has a property of unabsorbing ultraviolet light. In addition, as described above, the measurement device 1 normally uses light having the wavelength range of the ultraviolet light as the excitation light. Hence, since the quartz appropriately transmits the excitation light, the quartz is considered to be appropriate as a material of the protective member.

However, when an intensity of the fluorescence is allowed to be lowered to a certain extent, the protective member may be made of a glass material or a light-transmitting resin material. Here, in a case where a resin-based material is used as the material of the protective member, a material having no negative effect on the measurement target site (surface of the skin of a human body) needs to be selected.

As described above, the quartz plate 15 is detachably provided in the opening of the sleeve 16. Therefore, whenever the subjects are replaced, it is possible to remove and replace the quartz plate 15 from the front end surface 14I.

Therefore, since the measurement is performed by using a new quartz plate 15 for each subject, it is possible to reduce contamination of the front end surface 14I and a risk of infection due to the contamination. Hence, it is possible to easily secure hygiene by using the measurement probe 10.

(Configuration of Measurement Probe 10c as Comparative Example)

Next, a configuration of a measurement probe 10c as a comparative example of the measurement probe 10 of the embodiment is described with reference to FIGS. 5(a) and 5(b).

FIG. 5(a) is a view similar to FIG. 1(a), and illustrating a state in which the fingertip 90 is placed on the measurement base 121. In addition, FIG. 5(b) is a view similar to FIG. 1(b), and an enlarged view illustrating the vicinity of the front end surface 14cI of the measurement probe 10c in FIG. 5(a).

The measurement probe 10c has a configuration that is realized by removing the quartz plate 15 from the measurement probe 10 of Embodiment 1.

Similarly to the measurement probe 10 of Embodiment 1, in the measurement probe 10c, the front end of the sleeve 16 projects from the front end surface 14cI. Therefore, when the sleeve 16 and the fingertip 90 come into contact with each other, a gap 95c is defined between the front end surface 14cI and the fingertip 90.

The gap 95c causes the front end surface 14cI and the fingertip 90 to be spatially separated from each other. Therefore, similarly to the measurement probe 10 of Embodiment 1, it is possible for the front end surface 14cI to be kept clean.

(Problem Likely Arising in Measurement Probe 10c as Comparative Example)

Subsequently, a problem that can arise in the measurement probe 10c as the comparative example is described with reference to FIG. 6. The problem is newly found through study by the inventors of the present application.

Figure 6:
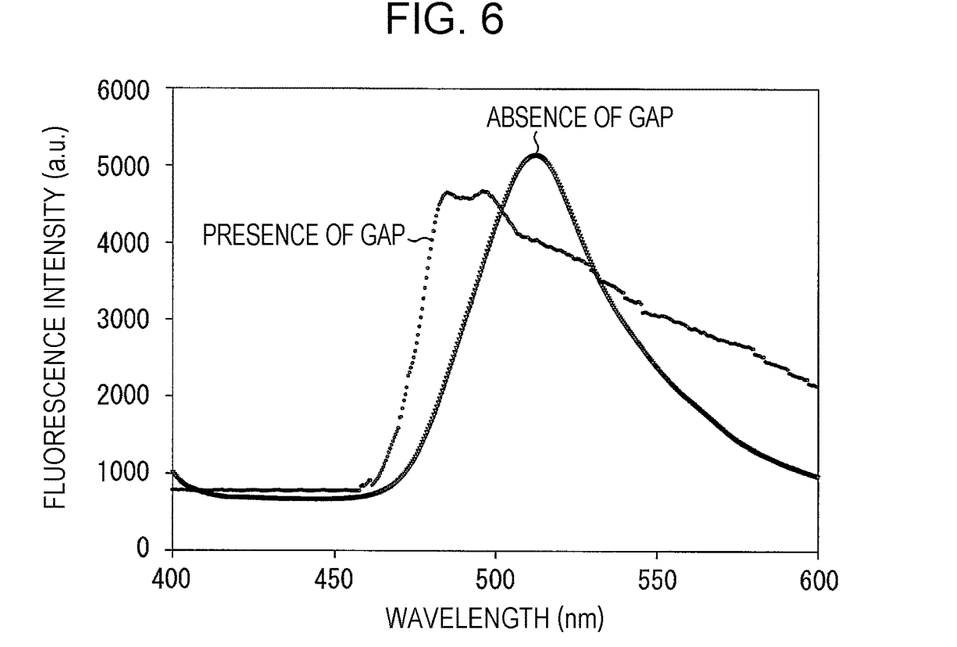
FIG. 6 is a graph illustrating a waveform (spectrum) of a fluorescence intensity obtained in a case where a measurement probe of the related art measures a subject and a waveform of a fluorescence intensity obtained in a case where the measurement probe as the comparative example measures a subject, respectively.

FIG. 6 is a graph illustrating a waveform (spectrum) of a fluorescence intensity obtained in a case where a measurement probe of the related art measures a subject (fluorescence plate) and a waveform of a fluorescence intensity obtained in a case where the measurement probe 10c measures a subject, respectively.

In the graph in FIG. 6, the horizontal axis represents a wavelength and the vertical axis represents a fluorescence intensity. A unit of the horizontal axis is nm and a unit of the vertical axis is an arbitrary unit (a.u.).

As described above, in the case where the measurement probe 10c measures the subject, the gap 95c causes the front end surface 14cI and the subject to be spatially separated from each other. On the other hand, in a case where the measurement probe of the related art measures the subject, the front end surface of the measurement probe and the measurement target site are in direct contact with each other.

In other words, the measurement by the measurement probe of the related art corresponds to a measurement performed in a case where a gap is not present. FIG. 6 illustrates the measurement result as a graph of "absence of gap". On the other hand, the measurement by the measurement probe 10c corresponds to a measurement performed in a case where a gap is present. FIG. 6 illustrates the measurement result as a graph of "presence of gap".

In the measurement result (the measurement result obtained by the measurement probe of the related art) illustrated in the graph of "absence of gap", a peak wavelength of the fluorescence intensity was found around a wavelength of 510 nm. In addition, a waveform of the fluorescence intensity having small distortion was obtained.

On the other hand, in the measurement result (the measurement result obtained by the measurement probe 10c) illustrated in the graph of "presence of gap", the peak wavelength of the fluorescence intensity was found around a wavelength of 490 nm. In addition, a waveform of the fluorescence intensity having large distortion was obtained.

In other words, in the measurement performed in the case where the gap is present, it was obvious that problems arise in that (i) the peak wavelength of the fluorescence intensity was shifted, and (ii) the waveform of the fluorescence intensity had the distortion, compared to the measurement performed in the case where the gap is absent.

The problems arise because, in the measurement probe 10c, the gap 95c is present (i) on a light path of the excitation light radiating from the front end surface 14cI toward the inside of the subject (the inside of the living body in practice) and (ii) on a light path of the fluorescence from the inside of the subject and received in the front end surface 14cI. In other words, the refractive index of the gap 95c and the refractive index of the front end surface 14cI are significantly different from each other, and thereby light scattering or refraction causes stray light to be produced due to the difference between the refractive indexes.

Therefore, in the measurement by the measurement probe 10c, the stray light is produced due to the difference between the refractive indexes described above, and thereby a problem arises in that it is not possible to appropriately measure the waveform of the fluorescence intensity.

Note that, in general, the excitation light has a short wavelength as described above. Therefore, a relative delay at a propagating speed of the excitation light is considered as a factor of degradation of measurement accuracy.

(Advantageous Effects of Measurement Probe 10)

Figure 7:
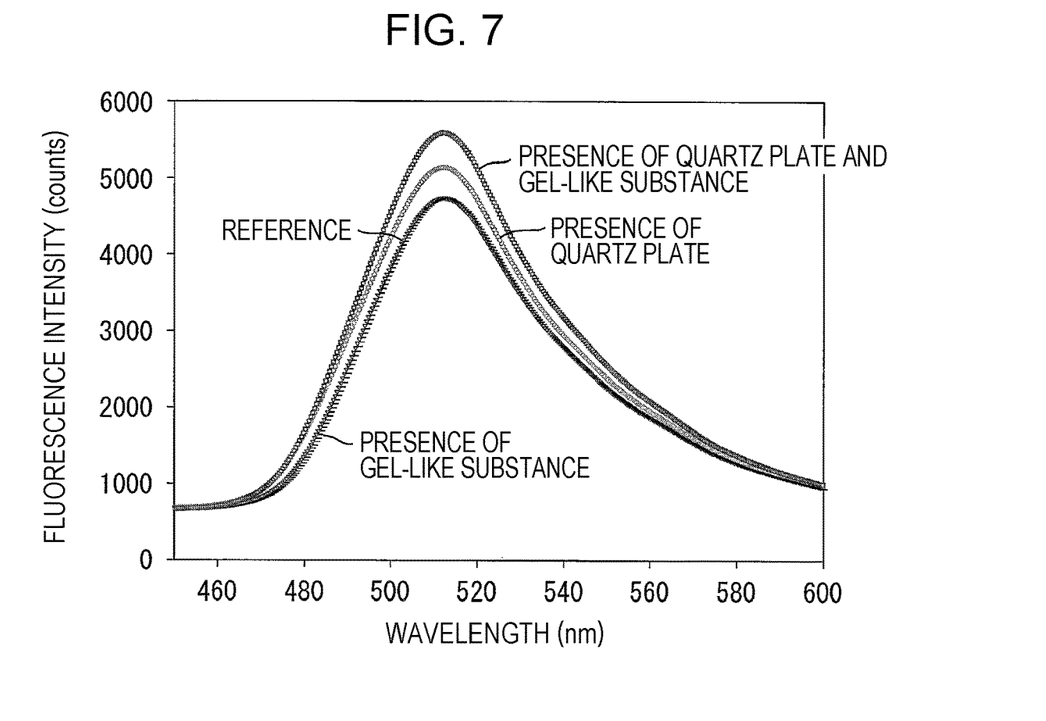
FIG. 7 is a graph illustrating waveforms of fluorescence intensities obtained in a case where a subject (fluorescent plate) is measured under various measurement conditions.

Subsequently, effects of the measurement probe 10 of the embodiment are described with reference to FIG. 7. FIG. 7 is a graph illustrating waveforms of fluorescence intensities obtained in a case where a subject (fluorescent plate) is measured under various measurement conditions.

In the graph in FIG. 7, the horizontal axis represents a wavelength and the vertical axis represents a fluorescence intensity. A unit of the horizontal axis is nm and a unit of the vertical axis is counts.

In FIG. 7, a graph illustrated as "reference" illustrates a waveform of a fluorescence intensity obtained in the case where the measurement probe of the related art measures the subject.

In addition, a graph illustrated as "presence of quartz plate" illustrates a waveform of a fluorescence intensity obtained in the case where the measurement probe 10 measures the subject. Note that, in the measurements in FIG. 7, the thickness of the quartz plate 15 was 0.5 mm.

Note that a graph illustrated as "presence of gel-like substance" and a graph illustrated as "presence of quartz plate and gel-like substance" are described in Embodiment 3 to be described below.

The measurement device 1 was used in the measurement of each graph illustrated in FIG. 7. NCSU033B(T) (manufactured by Nichia Corporation) was used as the light source 101, and SEC-2000 (manufactured by ALS Co., Ltd.) was used as the detector 102. In addition, a light intensity of the excitation light was 253 mW/cm$^2$. In addition, the fluorescence plate as the subject is formed of a standard sample of which the fluorescence intensity is not reduced over time.

As shown with the graph of "reference" in FIG. 7, in the case where the measurement probe of the related art measures the subject, similarly to FIG. 6, a wavelength of a fluorescence intensity having a peak around a waveform of 510 nm and having small distortion is obtained.

Further, as shown with the graph of "presence of quartz plate" in FIG. 7, in the case where the measurement probe 10 measures the subject, similarly to the graph of "reference", the peak wavelength of the fluorescence intensity was found around a wavelength of 510 nm. In addition, the waveform of the fluorescence intensity having small distortion was obtained.

In other words, according to the measurement probe 10 having the configuration in which the fingertip 90 as the measurement target site and the front end surface 14I are separated from each other, with an object to be hygienically used, it is possible to appropriately measure the waveform of the fluorescence intensity, similarly to the measurement probe of the related art.

This is because, as described above, the quartz plate 15 provided on the front end surface 14I of the measurement probe 10 has the refractive index higher than the air. Since the difference between the refractive index of the quartz plate 15 and the refractive index of the front end surface 14I is relatively small, the stray light is less produced in the configuration on the light path between the front end surface 14I and the subject.

Hence, according to the measurement probe 10 of the embodiment, the effects are achieved in that (i) it is possible to easily secure hygiene, and (ii) it is possible to reduce the stray light produced on the light path between the front end surface 14I and the subject.

Note that the graph of "presence of quartz plate" in FIG. 7 is obtained as the measurement result obtained in a state in which a surface state, a measurement position, and a contact state between the subject and the top surface of the quartz plate 15 are carefully considered such that an air layer is not interposed, reduced to the smallest extent, between the subject and the top surface (surface closest to the measurement target site) of the quartz plate 15.

Therefore, the graph of "presence of quartz plate" in FIG. 7 is considered as a measurement result obtained in a case where the effects of the stray light produced due to the presence of the air layer are particularly appropriately reduced. As described above, the quartz plate 15 is provided, and thereby it is possible to appropriately measure the waveform of the fluorescence intensity.

In addition, in the graph of "presence of quartz plate" in FIG. 7, higher fluorescence intensity is obtained, compared to the graph of "reference". This is considered to be because the quartz plate 15 having the refractive index higher than the air fulfils a function of an optical member that collects light under the measurement conditions described above.

In other words, since the quartz plate 15 is present and is able to collect the fluorescence that travels toward the front end surface 14I from a wider range of an angle, compared to a case where the quartz plate 15 is not present.

However, in a case where the quartz plate 15 had a thickness thicker than or equal to a certain degree, the fluorescence intensity to be measured was experimentally confirmed to be lowered. For example, in a case where the quartz plate 15 had a thickness of 2.0 mm, the fluorescence intensity was experimentally confirmed to be lowered to about 40%, compared to the graph of "reference".

Therefore, the thickness of the quartz plate 15 is preferably considered to be thinner than or equal to a certain value (for example, 2.0 mm or thinner). The upper limit value of the thickness may be appropriately determined, based on the experimental data of the measured intensity, depending on optical specifications of the measurement probe 10.

Embodiment 2

Figure 8:
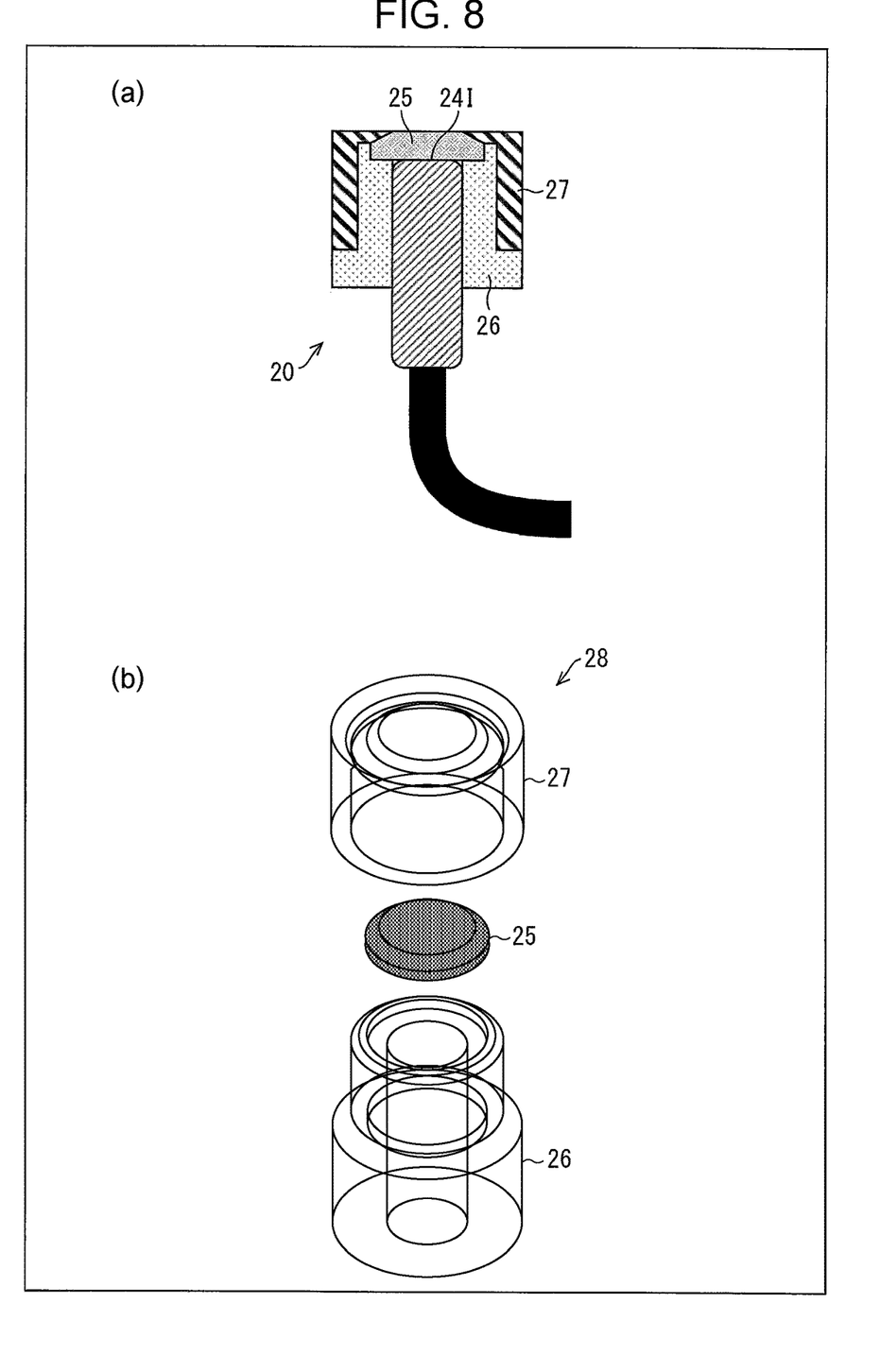
FIG. 8(a) is an enlarged diagram of the vicinity of a front end surface of the measurement probe.
FIG. 8(b) is an exploded diagram illustrating an assembly of an attachment mechanism of the measurement probe.

Another embodiment of the present invention is described on the basis of FIG. 8, as follows. Note that, for convenience, the same reference signs are assigned to the members described in the embodiment described above and the members having the same functions, and description thereof is omitted.

(Detailed Configuration of Measurement Probe 20)

Next, a detailed configuration of the measurement probe 20 is described with reference to FIGS. 8(*a*) and 8(*b*). FIG. 8(*a*) is an enlarged view illustrating the vicinity of a front end surface 24I of the measurement probe 20. In addition, FIG. 8(*b*) is an exploded view of an assembly of an attachment mechanism of the measurement probe 20.

The measurement probe 20 includes a quartz plate 25 (protective member), a sleeve 26 (support member, that is, a first support member), and a cap 27 (support member, that is, a second support member).

The quartz plate 25 is provided to come into contact with the front end surface 24I. Similarly to the quartz plate 15 of Embodiment 1, the quartz plate 25 serves as a protective member that protects the front end surface 24I during the contact with the measurement target site. In the embodiment, the quartz plate 25 has a substantially disc shape with a diameter of 5 mm and a thickness of 1 mm.

In addition, the sleeve 26 is provided at the front end portion of the measurement probe 20 so as to surround a part of the front end surface 24I in the circumferential direction. The sleeve 26 is provided with an opening in which the quartz plate 25 is detachably mounted.

Further, the cap 27 is provided on the front end portion of the measurement probe 20 so as to cover the entire front end surface 24I in the circumference direction, and the top surface (surface closest to the measurement target site) of the sleeve 26. The front end of the cap 27 projects from the front end surface 24I.

The cap 27 is disposed to be movable with respect to the sleeve 26 and serves as fixing a relative positional relationship between the quartz plate 25 and the sleeve 26. The sleeve 26 and the cap 27 may be made of a transparent acrylic material, for example.

In the measurement probe 20, the sleeve 26 and the cap 27 function as support members that support the quartz plate 25 in the circumferential direction of the opening. In the measurement probe 20, the cap 27 is provided as an additional support member, and thereby it is possible to more stably fix the quartz plate 25, compared to the measurement probe 10 of Embodiment 1.

Therefore, it is possible to prevent a positional shift of the quartz plate 25 also toward a direction opposite to the measurement probe 20. Therefore, it is possible to reduce a possibility that the measurement accuracy of the fluorescence will be lowered due to an orientation of the measurement target site. In other words, even in a case where the front end surface 24I faces any direction, it is possible to appropriately perform the measurement.

Further, the cap 27 is present, and thereby it is possible to reduce a possibility that a local air layer (gap) is interposed on an interface between the quartz plate 25 and the front end surface 24I. In this manner, it is possible to reduce an occurrence of the stray light.

In addition, in order to more reduce the occurrence of the stray light, it is preferable that the quartz plate 25 come into contact with a surface of the measurement target site such that the local air layer is not interposed on the interface between the quartz plate 25 and the measurement target.

Therefore, it is preferable that a structure of the measurement probe 20 be provided such that (i) the top surface of the quartz plate 25 flushes with the top surface of the cap 27, or (ii) the top surface of the quartz plate 25 projects from the top surface of the cap 27.

In addition, the quartz plate 25 is provided with an inclined structure (tapered shape) on an outer edge portion of the quartz plate. Similarly, also in the cap 27, the cap 27 also has a tapered shape on an inner edge portion such that the cap is able to engage with the end portion of the quartz plate 25.

In other words, inclined surfaces that are inclined at an angle corresponding to each other are formed on the outer edge portion of the quartz plate 25 and the inner edge portion of the cap 27. More specifically, the inclined surfaces are formed on the outer edge portion of the quartz plate 25 and on the inner edge portion of the cap 27, respectively, and an angle between the inclined surfaces is defined such that the quartz plate 25 and the cap 27 come into contact (close contact) with each other on the inclined surface.

In this manner, since the quartz plate 25 and the cap 27 reliably engage with each other, it is possible to more stably fix the quartz plate 25.

Note that, in a case where the cap 27 is not provided, an inclined surface for engaging with the end portion of the quartz plate 25 may be provided on the inner edge portion of the sleeve 26.

Further, as illustrated in FIG. 8(b), the sleeve 26, the quartz plate 25, and the cap 27 are assembled in this order from the lower side, and thereby an attachment mechanism 28 that is attachable to and detachable from the front end portion of the measurement probe 20 may be configured.

Note that, in the case where the cap 27 is not provided, the attachment mechanism may be configured by assembling the sleeve 26 and the quartz plate 25.

Similarly to the quartz plate 15 of Embodiment 1, whenever the subjects are replaced, it is also possible to remove and replace the attachment mechanism 28 from the front end portion of the measurement probe 20. Therefore, since it is possible to perform the measurement by using a new attachment mechanism 28 for each subject, it is possible to easily secure the hygiene.

In particular, since the cap 27 is also replaced at the same time as the replacement of the attachment mechanism 28, it is possible to secure hygiene of the top surface of the cap 27 which can come into contact with the measurement target site.

In addition, an operation of replacement of the attachment mechanism 28 is easier than an operation of the replacement of the quartz plate 15. Therefore, an advantage is achieved in that convenience of the measurement probe 20 for a user is improved. Hence, the measurement probe 20 may be delivered to the user with only the attachment mechanism 28 as a replacement part.

Embodiment 3

Figure 9:
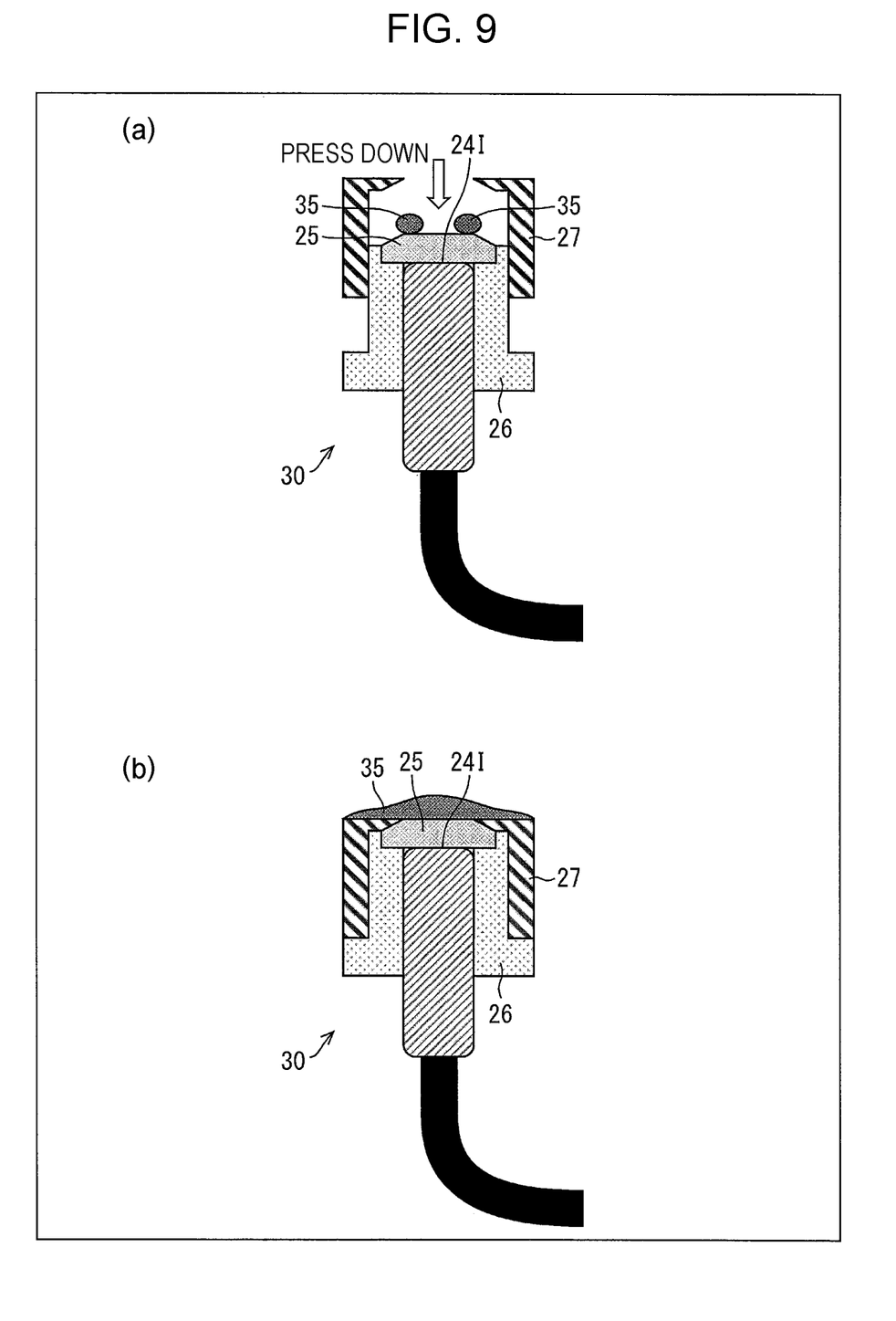
FIG. 9(a) is a diagram illustrating a state before a cap fixes a quartz plate.
FIG. 9(b) is a diagram illustrating a state after the cap fixes the quartz plate.

Another embodiment of the present invention is described on the basis of FIG. 9, as follows. Note that, for convenience, the same reference signs are assigned to the members described in the embodiment described above and the members having the same functions, and description thereof is omitted.

(Detailed Configuration of Measurement Probe 30)

Next, a detailed configuration of the measurement probe 30 of the embodiment is described with reference to FIGS. 9(a) and 9(b). The measurement probe 30 of the embodiment has a configuration that is realized by further adding a gel-like substance 35 (viscous material, that is, a filler) to the measurement probe 20 of Embodiment 2.

FIG. 9(a) is an enlarged view illustrating the vicinity of a front end surface 24I of the measurement probe 30, and illustrating a state before the cap 27 fixes the quartz plate 25. In addition, FIG. 9(b) is a view illustrating a state after the cap 27 fixes the quartz plate 25.

As illustrated in FIG. 9(a), the gel-like substance 35 is disposed on the quartz plate 25. FIG. 9(a) illustrates a configuration in which two grain-shaped gel-like substances 35 are disposed in the vicinity of the outer edge of the quartz plate 25 in the circumferential direction.

As illustrated in FIG. 9(b), in order to fix the quartz plate 25, the cap 27 is pressed down, and thereby the gel-like substance 35 is pushed down by the cap 27. In this manner, the gel-like substance 35 expands over the entire top surface of the quartz plate 25. The measurement performed by the measurement probe 30 is performed in the state illustrated in FIG. 9(b).

(Gel-Like Substance 35)

The gel-like substance 35 is a member having a viscosity which is provided to reduce the occurrence of the stray light in the measurement probe 30. An example of the gel-like substance 35 includes a material having low viscosity which is made of mainly water. Values of the viscosity of the gel-like substance 35 are 70,000 cP (centipoise) to 450,000 cP, and preferably from 70,000 cP to 150,000 cP. In addition, the value is preferably about 100,000 cP.

In addition, the refractive index of the gel-like substance 35 more approximates to the refractive index of the quartz plate 25 than to the refractive index of the air. Hereinafter, functions of the gel-like substance 35 will be described.

In a case where the quartz plate 25 has a high stiffness and measures a site having a curved surface such as the skin as the measurement target site, the air layer (gap) is likely to be formed between the measurement target site and the quartz plate.

For example, in the case where the measurement is performed on the fingertip 90 as the measurement target site, a possibility that the air layer will be formed between a first joint portion and the quartz plate 25 is considered. In addition, in the case where the fingertip 90 has a wound, a possibility that the air layer will be formed between the wound portion and the quartz plate 25 is considered. Therefore, as described above, there is a concern that the stray light will be produced due to the local air layer interposed therebetween.

In the measurement probe 30 of the embodiment, the gel-like substance 35 having a viscosity flows into the air layer between the measurement target site and the quartz plate 25. Therefore, the air layer is filled with the gel-like substance 35, and thereby it is possible to prevent the local air layer from being formed.

In the embodiment, echo jelly manufactured by Hitachi Aloka Medical Ltd. is used as the gel-like substance 35. Note that a gel pad such as sonagel manufactured by Takiron Co., LTD. may be used as the gel-like substance 35.

In addition, silicone rubber, silicone oil, or the like may be used as the gel-like substance 35. In other words, the gel-like substance 35 has (i) the refractive index closer to the refractive index of the quartz plate 25 than to the refractive index of the air, and (ii) is formed of a filler (material having a viscosity to the extent that the material can fill the air layer) that can fill the air layer in the case where the air layer is formed between a surface of the measurement target site and a surface of the quartz plate 25. If the conditions are satisfied, the value of the viscosity of the gel-like substance 35 does not need to be within the range described. However, when the contact of the gel-like substance 35 with the measurement target site (surface of the skin of a human body) is considered, it is preferable that echo jelly that does not have a negative effect on the skin be used as the gel-like substance 35.

The embodiment employs a configuration in which the cap 27 presses the gel-like substance 35, and thereby the gel-like substance 35 expands over the top surface of the quartz plated 25. In this manner, the gel-like substance 35 is disposed to cover the top surface of the quartz plate 25.

Note that the top surface of the quartz plate 25 may be covered with the gel-like substance 35 in another method. For example, the gel-like substance 35 may be applied on the quartz plate 25 in advance.

In addition, the gel-like substance 35 is applied on the measurement target site, and thereby the gel-like substance 35 may cover the top surface of the quartz plate 25 when the top surface of the quartz plate 25 and the measurement target site come into contact with each other.

Note that it is preferable that the top surface of the quartz plate 25 be formed to have an area larger than or equal to a certain degree so as to be covered with the gel-like substance 35. In addition it is preferable that the top surface of the quartz plate 25 be formed to have a flat surface so as to be covered with the gel-like substance 35.

Hereinafter, a case of using the echo jelly as the gel-like substance 35 will be described. In general, the echo jelly is applied on the skin of the subject such that a propagation property of ultrasonic waves is improved, during diagnosis using the ultrasonic waves.

Since characteristic acoustic impedance of the air is smaller about 3600 times than water, the propagation property of the ultrasonic waves (sound transmittance) is degraded due to a difference between the characteristic acoustic impedance with another substance.

The echo jelly contains water as a main component (about 70 to 80%), 15% of glycerine or the like, and 1% or less of methyl parahydroxybenzoate. Therefore, the echo jelly as a jelly-like substance having the characteristic acoustic impedance approximate to that of a living body is applied on the skin of the subject, and thereby the propagation property of the ultrasonic waves is improved between the ultrasonic probe and the inside of the body of the subject.

In this respect, in the embodiment, in order to reduce an occurrence of the stray light due to the difference between the refractive indexes of light, the echo jelly is used.

Here, specific values of absolute refractive indexes of the substances contained in the echo jelly are as follows.

| | |
|---|---|
| air (0° C., 1 atmosphere) | 1.000292 |
| water (20° C.) | 1.3334 |
| quartz glass | 1.543 |
| glycerine | 1.4746 |

Therefore, the difference between the refractive indexes of the echo jelly and the quartz plate 25 is smaller than the difference between the refractive indexes of the air and the quartz plate 25. Hence, in a case where the measurement probe 30 performs the measurement, the echo jelly is applied to the measurement target site, and thereby the occurrence of the stray light is reduced. Thus, the measurement probe 30 performs the measurement with improved accuracy.

As described above, the echo jelly is the substance that has been originally used to secure the propagation property of the ultrasonic waves in the ultrasonic diagnosis. Hence, the original use (that is, objectives and effects) of the echo jelly is different from the gel-like substance 35 described above.

However, in order to reduce the occurrence of the stray light produced in the measurement probe 30, the inventors of the present application find that it is possible to use the echo jelly as the gel-like substance 35 that covers the top surface of the quartz plate 25.

Note that the gel-like substance 35 may be formed to have a capsule shape. In addition, the measurement probe 30 may have a configuration in which it is possible to inject the gel-like substance 35 over the top surface of the quartz plate 25 from a side of the cap 27.

(Effects of Measurement Probe 30)

Subsequently, effects of the measurement probe 30 of the embodiment are described with reference to FIG. 7.

In FIG. 7, a graph illustrated as "presence of gel-like substance" illustrates the waveform of the fluorescence intensity obtained in the case where the echo jelly is applied on the front end surface (contact surface with the measurement target site) of the measurement probe of the related art, and the measurement probe of the related art measures the subject.

In addition, a graph illustrated as "presence of quartz plate and gel-like substance" illustrates a waveform of the fluorescence intensity obtained in the case where the measurement probe 30 measures the subject. Note that, in the measurements in FIG. 7, the thickness of the quartz plate 25 was 0.5 mm.

As illustrated in the graph of "presence of gel-like substance" in FIG. 7, in the case where the echo jelly is applied on the front end surface of the measurement probe, substantially the same graph as the graph of "reference" is obtained. Hence, the echo jelly is applied on the front end surface of the measurement probe, and thereby it is considered that the negative effect such as the reduction in the fluorescence intensity does not occur on the measurement.

Hence, according to the measurement probe 30 of the embodiment, the effects are achieved in that (i) it is possible to easily secure hygiene, and (ii) it is possible to reduce the occurrence of the stray light produced on the light path between the front end surface 24I and the subject due to the air layer.

In addition, the gel-like substance 35 is used, and thereby the quartz plate 25 does not need to have a specific shape such that a volume of the air layer between the quartz plate 25 and the measurement target site is reduced. Therefore, for example, the top surface of the quartz plate 25 does not need to have a curved lens shape. In this manner, it is possible to reduce costs in design and manufacturing of the quartz plate 25.

Note that, in the graph of "presence of quartz plate and gel-like substance" in FIG. 7, higher fluorescence intensity is obtained, compared to the graph of "presence of gel-like substance". This is considered to be because the quartz plate 25 fulfils a function of an optical member that collects light.

Embodiment 4

Note that the configuration that is realized by further adding the gel-like substance 35 to the measurement probe is not necessarily limited to the configuration of the measurement probe 30 of Embodiment 3.

For example, the measurement probes may be realized by configurations illustrated in FIGS. 10(a) and 10(b), respectively.

FIG. 10(a) is a diagram illustrating a detailed configuration of a measurement probe 30a as a first example of the measurement probe of the embodiment. In addition, FIG. 10(b) is a diagram illustrating a detailed configuration of a measurement probe 30b as a second example of the measurement probe of the embodiment.

Note that the measurement probe 30a may be understood as a first modification example of the measurement probe 30 of Embodiment 3. In addition, the measurement probe 30b may be understood as a second modification example of the measurement probe 30 of Embodiment 3.

The measurement probe 30a has a configuration that is realized by (i) replacing the quartz plate 25 with the quartz plate 15 of the measurement probe 10 of Embodiment 1, and (ii) replacing the cap 27 with the cap 37, in the measurement probe 30.

Since the quartz plate 15 is not provided to have the tapered shape on the outer edge portion, the cap 37 is also formed to have a shape without the tapered shape on the inner edge portion.

In addition, the measurement probe 30b has a configuration that is realized by (i) replacing the sleeve 26 with the sleeve 16 of Embodiment 1, and (ii) removing the cap 37, in the measurement probe 30a.

In other words, the measurement probe 30b has a configuration that is realized by further adding the gel-like substance 35 to the measurement probe 10 of Embodiment 1.

The quartz plate 15 and the gel-like substance 35 are also provided in the measurement probes 30a and 30b, and thereby it is possible to appropriately reduce the occurrence of the stray light.

Modification Example

Figure 10:
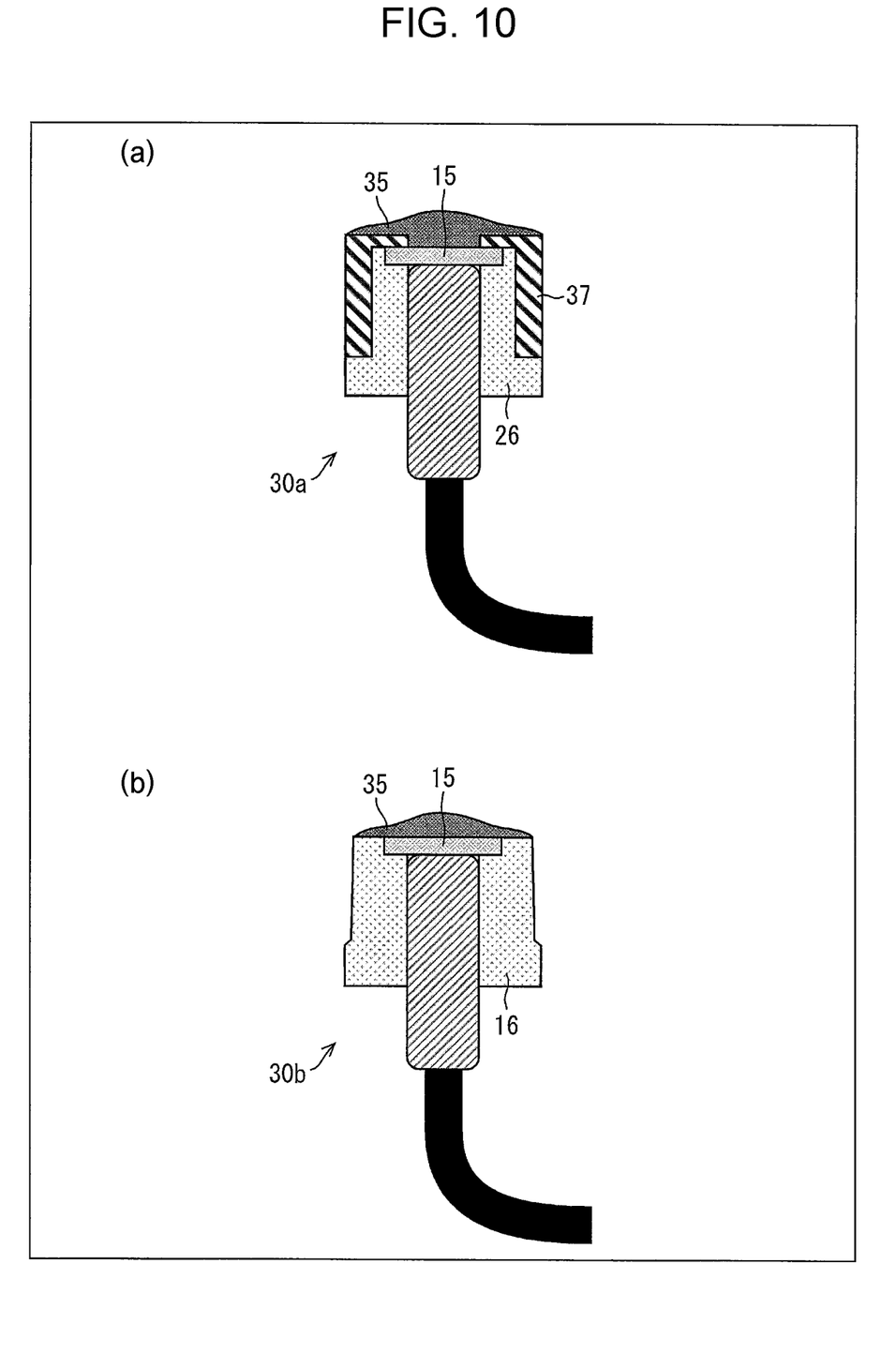
FIG. 10(a) illustrates a first example.
FIG. 10(b) illustrates a second example.

Note that since the cap (27 or 37) fixes the quartz plate (25 or 15) in Embodiments 3 and 4 described above, the air layer that is a factor of causing the stray light is difficult to be formed in the contact portion between the quartz plate and the front end surface of the measurement probe.

However, in order to reliably reduce an occurrence of forming of the air layer, the interface, on which the quartz plate and the front end surface of the measurement probe come into contact with each other, may be covered with the gel-like substance 35.

APPENDIX

The present invention is not limited to the embodiments described above, it is possible to perform various modifications within a range of the claims, and an embodiment obtained by appropriately combining technical units described in different embodiments, respectively, is also included in a technical range of the invention. Further, it is possible to combine the technical units described in the embodiments, respectively, and it is possible to form a new technical feature.

INDUSTRIAL APPLICABILITY

The present invention can be applied to a measurement probe that receives fluorescence emitted from a fluorescent material in a biological sample.

REFERENCE SIGNS LIST 1 measurement device
10, 20, 30, 30a, 30b measurement probe
11 light incoming fiber (light-receiving portion)
12 light emitting fiber (radiating portion)
14I front end surface
15, 25 quartz plate (protective member)
16, 26 sleeve (support member, first support member)
27, 37 cap (support member, second support member)
28 attachment mechanism
35 gel-like substance (filler)
90 fingertip (biological sample)
101 light source
102 detector (detecting unit)

The invention claimed is:
1. A measurement probe that receives fluorescence emitted by radiation of excitation light to a biological sample, the measurement probe comprising:
a radiating portion that radiates the excitation light;
a light receiving portion that receives the fluorescence;
a support member disposed at a front end portion of the radiating portion or the light-receiving portion; and a transparent protective member disposed at a front end surface of the radiating portion or the light-receiving portion, wherein the support member is provided with an opening in which the transparent protective member is detachably mounted, the support member includes
- a first support member that is disposed on the front end portion, and
- a second support member that is disposed to be movable with respect to the first support member and fixes a relative positional relationship between the transparent protective member and the first support member, and inclined surfaces are formed on an outer edge portion of the transparent protective member and on an inner edge portion of the second support member, respectively, and an angle between the inclined surfaces is defined such that the transparent protective member and the second support member come into contact with each other on the inclined surfaces.

2. The measurement probe according to claim 1,
wherein in a case where a filler, which is capable of filing a gap formed between a surface of the transparent protective member and a surface of the biological sample, fills the gap,
the transparent protective member has a refractive index higher than air, and
the refractive index of the filler is more approximate to a refractive index of the transparent protective member than to the refractive index of the air.

3. The measurement probe according to claim 1,
wherein the transparent protective member is a quartz plate.

4. A measurement device comprising:
the measurement probe according to claim 1;
a light source that emits the excitation light; and
a detector that detects a fluorescence intensity of a wavelength of the fluorescence.

5. An attachment mechanism which is provided to a measurement probe that receives fluorescence emitted by radiation of excitation light to be a biological sample, the measurement probe comprising:
a radiating portion that radiates the excitation light; and
a light receiving portion that receives the fluorescence,
the attachment mechanism comprising:
a transparent protective member; and
a support member,
wherein the attachment mechanism is detachably mounted at a front end portion of the radiating portion or the light-receiving portion,
the support member is disposed at the front end portion as a result of the attachment mechanism being mounted at the front end portion,
the transparent protective member is disposed at a front end surface of the radiating portion or the light-receiving portion as a result of the attachment mechanism being mounted at the front end portion,
the support member is provided with an opening in which the protective member is detachably mounted,
the support member includes
- a first support member that is disposed on the front end portion, and
- a second support member that is disposed to be movable with respect to the first support member and fixes a relative positional relationship between the transparent protective member and the first support member, and inclined surfaces are formed on an outer edge portion of the transparent protective member and on an inner edge portion of the second support member, respectively, and an angle between the inclined surfaces is defined such that the transparent protective member and the second support member come into contact with each other on the inclined surfaces.

\* \* \* \* \*